United States Patent
Findeisen (10) Patent No.: US 8,343,014 B2
(45) Date of Patent: Jan. 1, 2013

(54) REVERSIBLE TOE MANIPULATION DEVICE

(76) Inventor: Kurt Charles Findeisen, Los Angeles, CA (US)

( * ) Notice: Subject to any disclaimer, the term of this patent is extended or adjusted under 35 U.S.C. 154(b) by 0 days.

(21) Appl. No.: 12/966,626

(22) Filed: Dec. 13, 2010

(65) Prior Publication Data

US 2011/0077570 A1 Mar. 31, 2011

Related U.S. Application Data (63) Continuation-in-part of application No. 12/246,504, filed on Oct. 7, 2008, now abandoned.

(60) Provisional application No. 60/978,130, filed on Oct. 7, 2007.

(51) Int. Cl.
*A61F 5/00* (2006.01)
*A63B 23/00* (2006.01)

(52) U.S. Cl. ............ 482/47; 601/40; 602/21

(58) Field of Classification Search ............ 482/148, 482/79, 48–49; 601/40; 602/21
See application file for complete search history.

(56) References Cited

U.S. PATENT DOCUMENTS

| | | | |
|---|---|---|---|
| 892,412 A | 7/1908 | Farra | |
| 1,163,490 A | 12/1915 | Weil | |
| 1,373,211 A | 3/1921 | Tanner | |
| 1,624,171 A | 10/1925 | Johnson | |
| 1,930,413 A | 7/1930 | Bruel | |
| 1,785,185 A | 12/1930 | Day | |
| 2,471,997 A | 5/1949 | Baltor | |
| 2,506,308 A | 5/1950 | Maynier | |
| 2,603,212 A | 7/1952 | Zeve | |
| 2,740,207 A * | 4/1956 | Starensier | 602/31 |
| 2,949,112 A | 8/1960 | Murray | |
| 4,017,987 A * | 4/1977 | Perez et al. | 36/11.5 |
| 4,207,880 A * | 6/1980 | Zinkovich | 602/30 |
| 4,414,964 A | 11/1983 | Farino | |
| 4,877,018 A * | 10/1989 | Ikebe et al. | 602/30 |
| 5,062,625 A * | 11/1991 | Vonk | 482/48 |
| 5,076,263 A | 12/1991 | Funatogawa | |
| 5,925,008 A * | 7/1999 | Douglas | 602/22 |
| D439,704 S * | 3/2001 | Ikeda | D28/57 |
| 6,228,001 B1 * | 5/2001 | Johnson et al. | 482/48 |
| 6,238,357 B1 | 5/2001 | Kawaguchi | |
| 6,298,580 B1 * | 10/2001 | Tadayon | 36/11.5 |
| 6,481,443 B1 * | 11/2002 | Moore-Johnson et al. | 132/73 |
| 6,691,315 B1 * | 2/2004 | Clarke et al. | 2/20 |
| 6,817,967 B1 * | 11/2004 | Ott et al. | 482/48 |
| 6,981,283 B2 * | 1/2006 | Kujawski | 2/161.6 |
| 7,089,061 B2 * | 8/2006 | Grey | 607/63 |
| D595,897 S * | 7/2009 | Moldauer et al. | D28/56 |
| D600,818 S * | 9/2009 | Yang | D24/215 |
| D629,055 S * | 12/2010 | Findeisen | D21/685 |
| 2003/0073939 A1 * | 4/2003 | Taylor et al. | 601/40 |
| 2005/0177085 A1 * | 8/2005 | Green et al. | 602/30 |
| 2005/0251081 A1 * | 11/2005 | McClanahan et al. | 602/30 |
| 2007/0174998 A1 * | 8/2007 | Powell | 16/430 |

(Continued)

*Primary Examiner* — Stephen Crow (57) ABSTRACT

A reversible toe manipulation device comprising a separator for inserting between two toes of the human foot, the separator including a duality of shaped openings, each shaped opening adapted for receiving at least one toe and the shaped openings being from 0.25 to 2.0" in depth, at least one of the shaped openings fully attaching around one or more toes so that the separator is attached to the feet and toes, the separator further comprising an adjustable stretch width section that can be altered using a removable stretch width section to the width desired by the wearer, said adjustable stretch width section interposed between the shaped openings, the separator spreading the toes between 0.25 to 2.0" in width, such that when the toes are inserted into the shaped openings the toes are contactless.

11 Claims, 7 Drawing Sheets

U.S. PATENT DOCUMENTS

| | | | |
|---|---|---|---|
| 2007/0268268 A1* | 11/2007 | Allison | 345/173 |
| 2008/0276395 A1* | 11/2008 | Powell et al. | 15/143.1 |
| 2008/0276945 A1* | 11/2008 | Rosen | 128/864 |
| 2010/0037413 A1* | 2/2010 | Tyler | 15/244.4 |
| 2010/0304873 A1* | 12/2010 | Markowitz et al. | 463/47 |
| 2011/0030726 A1* | 2/2011 | Vaillancourt et al. | 134/6 |

* cited by examiner

REVERSIBLE TOE MANIPULATION DEVICE

RELATED APPLICATIONS

This application is a continuation in part that claims the benefit of and priority to U.S. Utility application Ser. No. 12/246,504 filed Oct. 7, 2008, now abandoned, which claims priority to U.S. Provisional Application Ser. No. 60/978,130 filed Oct. 7, 2007 and U.S. Design Patent Application 29/362,289 filed May 23, 2010 which claims the benefit of U.S. Utility application Ser. No. 12/246,504 filed Oct. 7, 2008 by Kurt Charles Findeisen the contents of which are hereby incorporated by reference as if recited in full herein for all purposes.

BACKGROUND

The proper health of feet and toes is vitally important to the overall quality and enjoyment of life. Foot and toe bone structure and malformation are the result of a combination of hereditary design, daily use, and age. In some instances, the constant use of ill-fitted shoes results in unnatural forces on certain portions of the feet and toes. In extreme cases, improper toe position or confinement will result in loss of blood circulation, which may lead to gangrene and/or amputation. Therefore the use of devices that passively manipulate the feet and toes to counteract any harmful forces are beneficial to the overall health of the human body.

Foot and toe ailments are common. The severity of such ailments can increase over time. A common foot and toe ailment is a bunion. A bunion is when the big toe of one or both feet becomes gradually malformed such that it angles inward towards the second toe and presses up against the second toe causing foot pain. A common treatment for a bunion is to insert a toe spacer in between the big toe and the second toe thus reducing the pressure and friction caused by the malformed toes. As a foot and toe pain relief product, the toe spacer is part of a group that includes products such as toe separators, bunion splints, toe guards, etc. These types of treatments are either worn only during waking hours under the wearer's footwear (toe spacer), or worn only during sleeping hours (bunion splint).

The period of sleep is one of the most advantageous periods during which assistive devices can be utilized to improve the health of a person. In particular, while sleeping, the feet and toes of an individual are usually exposed and not confined by footwear. Also, during the period of sleep in the privacy of an individual's home, the use of a toe manipulation device is unlikely to be viewed by other individuals. A bunion splint is a current foot pain relief product that is used only during sleep. This product is far too cumbersome to wear while the wearer is awake under footwear.

The field of toe manipulation devices includes U.S. Pat. No. 1,080,305 to Scholl, U.S. Pat. No. 1,163,490 to Weil, U.S. Pat. No. 1,624,171 to E. O. Johnson, U.S. Pat. No. 1,930,413 to Bruel, and U.S. Pat. No. 2,603,212 to Zeve. The inventive subject matter of these patents are all devices that are inserted between toes to provide spacing between toes that results in the correct position of the toes under the wearer's footwear. These five patents provide for devices that are not attached to the wearer's feet, and as such, are not intended to be used while the wearer is asleep. Even when used while the wearer is awake, these devices can become dislodged and thus are rendered useless because these devices are not attached to the wearer's toes. Additionally, these patents cover devices that are restricted to simply separating, rather than separating and/or stretching, the wearer's toes.

On the other hand, U.S. Pat. No. 2,506,308 to Maynier, U.S. Pat. No. 5,076,263 to Funatogawa, and U.S. Pat. No. 6,238,357 to Kawaguchi, et al. provide for devices that stretch most, if not all, of the wearer's toes. These devices can only be used while the wearer is not wearing footwear. They are far too cumbersome to be worn during sleep or under footwear while the wearer is awake. These devices are also limited to general foot and toe health improvement reached through stretching toes, not specific toe-related foot ailments that require focused direct attention.

U.S. Pat. No. 892,412 to E. S. Farra, U.S. Pat. No. 1,373,211 to F. T. Tanner, U.S. Pat. No. 1,785,185 to J. C. Day, and U.S. Pat. No. 4,414,964 to Farino, et al. provide for devices that are focused solely on correcting the position of the big toe. These devices are inflexible in terms of providing any spacing and/or stretching to any other toes of the foot. Except for the Farino, et al. inventive subject matter, these devices are also not reversible.

U.S. Pat. No. 2,471,997 to B. M. Baltor and U.S. Pat. No. 2,949,112 to A. E. Murray provide for devices that are intended to straighten or position, not stretch, the wearer's toes. These devices attach to all toes, and consequently, do not allow for any targeted relief to specific toes of a wearer's feet. Additionally, any device that attaches to all toes is more likely to become dislodged while the wearer sleeps than a device that attaches securely to one toe and rests in between two toes. As these devices are not intended to stretch any toes, they do not provide any sizing capabilities for desired spacing and/or stretching between toes.

None of the aforementioned prior art describe a reversible toe manipulation device constructed form that: 1. Has a shaped pliable material that is adjustable to enable varying degrees of separation, 2. Stays attached to the wearer's toes while the wearer is awake, wearing footwear or not, or asleep, and does not produce discomfort while the wearer is awake or asleep, and 3. Is capable of separating and/or stretching between any toes of a typical five-digit foot.

SUMMARY

The inventive subject matter overcomes the aforementioned problems by providing a reversible toe manipulation device that attaches to a wearer's toes and separates and/or stretches the space between specific toes whenever the wearer needs the benefits of such manipulation, whether it be while awake or asleep or both.

The inventive subject matter provides for a reversible toe manipulation device having a separator that is inserted between two toes, the separator including a duality of shaped openings, each shaped opening adapted for receiving at least one toe of the human foot and the shaped openings being from 0.25 to 2.0" in depth; the separator further comprising an adjustable stretch width section that includes a removable stretch width section that can be removed for sizing purposes, the adjustable stretch width section interposed between the shaped openings, the separator spreading the toes between 0.25 to 2.0" in width, such that when the toes are inserted into the shaped openings the toes are contactless. The reversible toe manipulation device is also fabricated from any pliable material that is safe to be worn against human skin. The reversible toe manipulation device is also fabricated from foam. The reversible toe manipulation device is also fabricated from foam that is polystyrene, polyurethane, extruded polyurethane, or copolymers. The reversible toe manipulation device is also fabricated from foam that is hydrophilic polyurethane. The reversible toe manipulation device is also fabricated from foam that is a non-irritant to the skin. The toe manipulation device also has holes that are circular in shape. The reversible toe manipulation device also has holes that are semi-circular in shape. The reversible toe manipulation device also has holes that are rectangular in shape.

This inventive subject matter relates to foot and toe manipulation devices. The various embodiments and domains described herein should not be construed as limitations in the potential application of the inventive subject matter. Rather they are teachings for the purpose of illustrating the ramifications and variations of possible embodiments of this inventive subject matter.

These and other embodiments are described in more detail in the following detailed descriptions and the figures.

The foregoing is not intended to be an exhaustive list of embodiments and features of the present inventive subject matter. Persons skilled in the art are capable of appreciating other embodiments and features from the following detailed description in conjunction with the drawings.

DRAWINGS

The following figures show embodiments according to the inventive subject matter unless noted as showing prior art. Closely related figures have the same number but different alphabetic suffixes.

REFERENCE NUMERALS IN THE DRAWINGS 10 shaped pliable material
12 shaped opening
14 removable shaped opening
16 adjustable stretch width section
18 removable stretch width section
20 removable stretch cut
22 half-circle indentation

DETAILED DESCRIPTION

Representative embodiments according to the inventive subject matter are shown in FIGS. 1 to 8, wherein similar features share common reference numerals. The specific embodiments are meant to be illustrative and not limiting of the scope of the inventive subject matter and the various ways it may be embodied.

For the purposes of reference, the term "the big toe" refers to the hallux and "the second toe" refers to the toe directly next to the hallux. These references are made for individuals with five toes on each foot.

In accordance with the present inventive subject matter, the reversible toe manipulation device has: 1. A shaped pliable material with, on one side, a shaped opening that passes fully through the pliable material with a removable shaped opening therein and, on the other side, a half-circle indentation that passes fully through the pliable material, and in between an adjustable stretch width section with a cut that passes fully through the pliable material creating a removable stretch width section.

Figure 1:
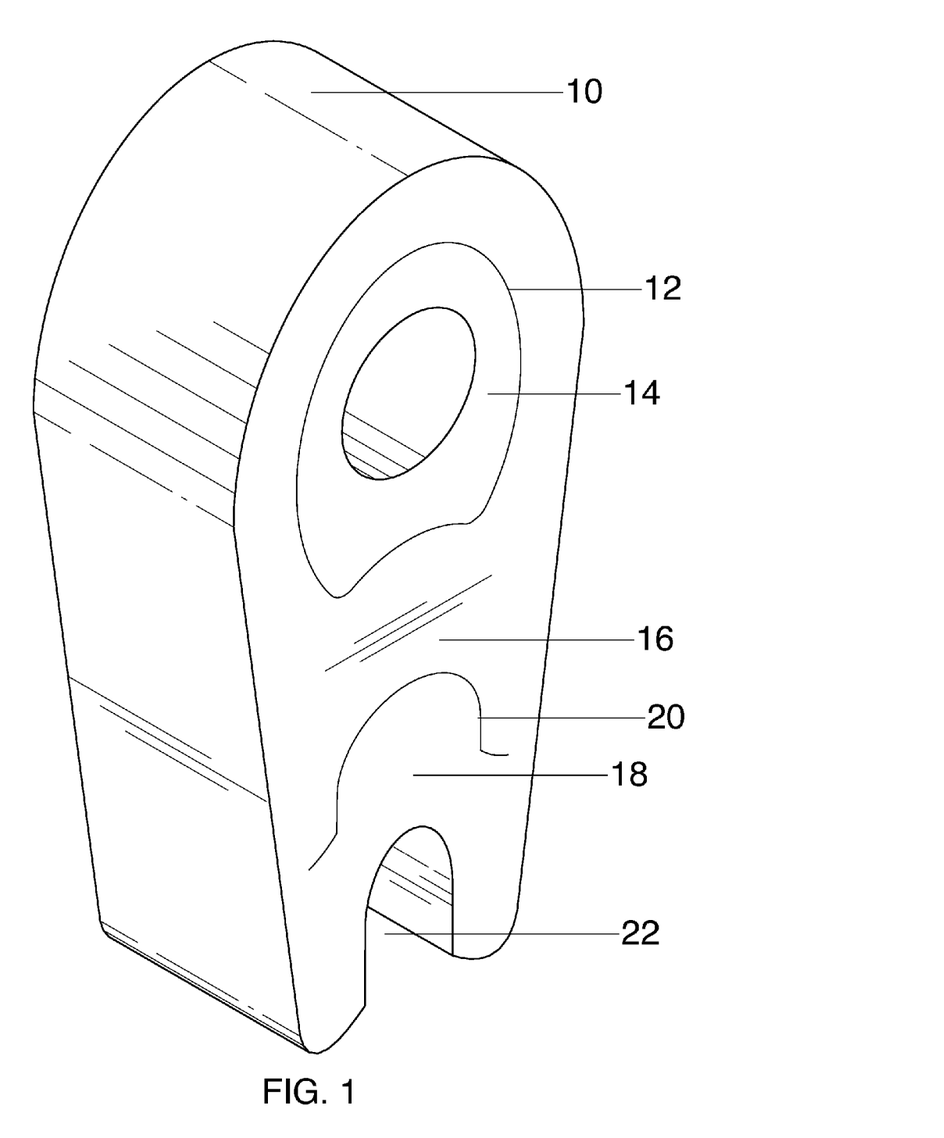
FIG. 1—Perspective view of the inventive subject matter.

Now referring to FIG. 1 that illustrates a side view of the inventive subject matter with a shaped pliable material 10 with a shaped opening 12, a removable shaped opening 14 therein, an adjustable stretch width section 16, a removable stretch width section 18, a removable stretch cut 20, and a half-circle indentation 22 on the opposite end of the shaped pliable material 10 from the shaped opening 12. For the purposes of this application, the term "width" shall refer to the dimension from the top of the device (reference character 10) to the bottom of the device (reference character 22). The term "depth" shall refer to the measure distance inside each shaped opening.

Figure 2:
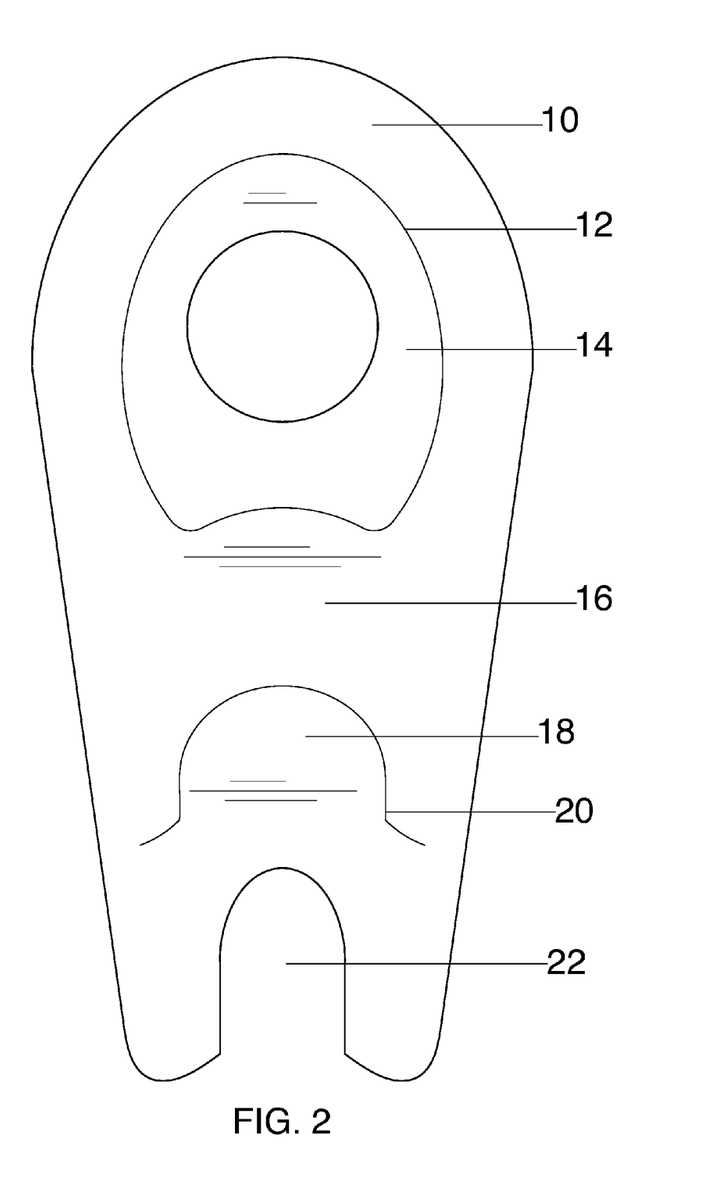
FIG. 2—Front view of the inventive subject matter.

Now referring to FIG. 2 that illustrates a front facing view of the inventive subject matter with a shaped pliable material 10 with a shaped opening 12, a removable shaped opening 14 therein, an adjustable stretch width section 16, a removable stretch width section 18, a removable stretch cut 20, and a half-circle indentation 22 on the opposite end of the shaped pliable material 10 from the shaped opening 12.

Figure 3:
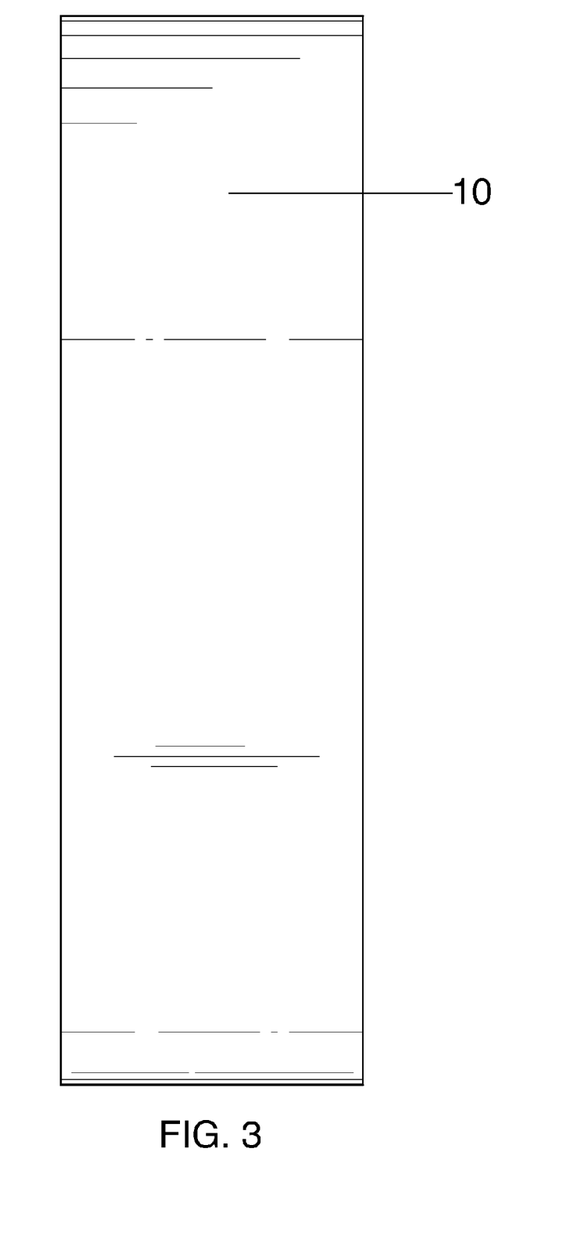
FIG. 3—Side view of the inventive subject matter.

Now referring to FIG. 3 that illustrates a side view of the inventive subject matter with a shaped pliable material 10.

Figure 4:
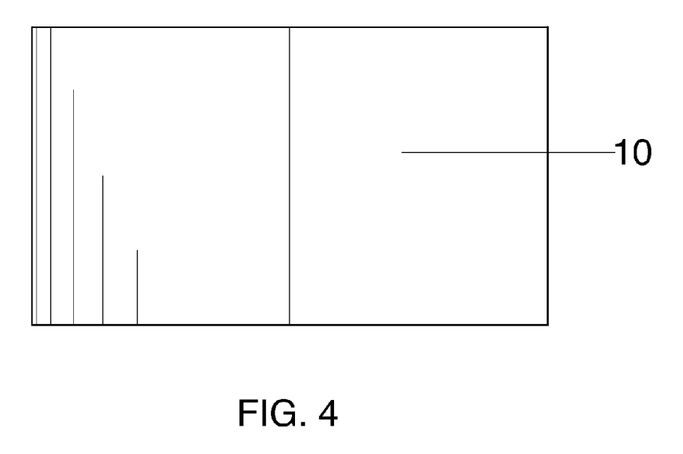
FIG. 4—Top view of the inventive subject matter.

Now referring to FIG. 4 that illustrates a top view of the inventive subject matter with a shaped pliable material 10.

Figure 5:
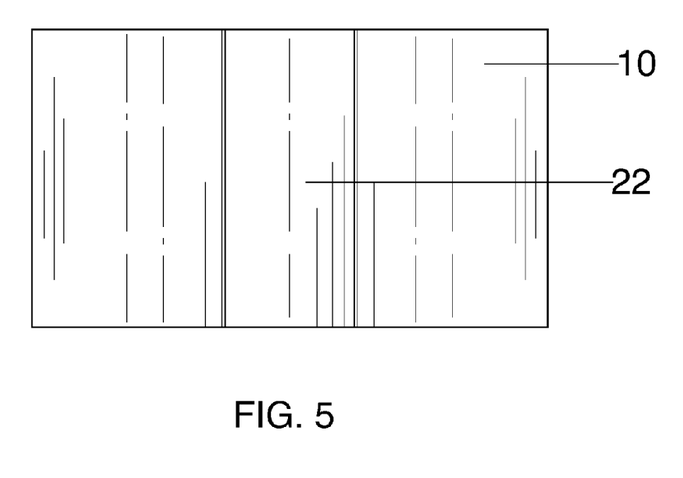
FIG. 5—Bottom view of the inventive subject matter.

Now referring to FIG. 5 that illustrates a bottom view of the inventive subject matter with a shaped pliable material 10 and a half-circle indentation 22.

Figure 6:
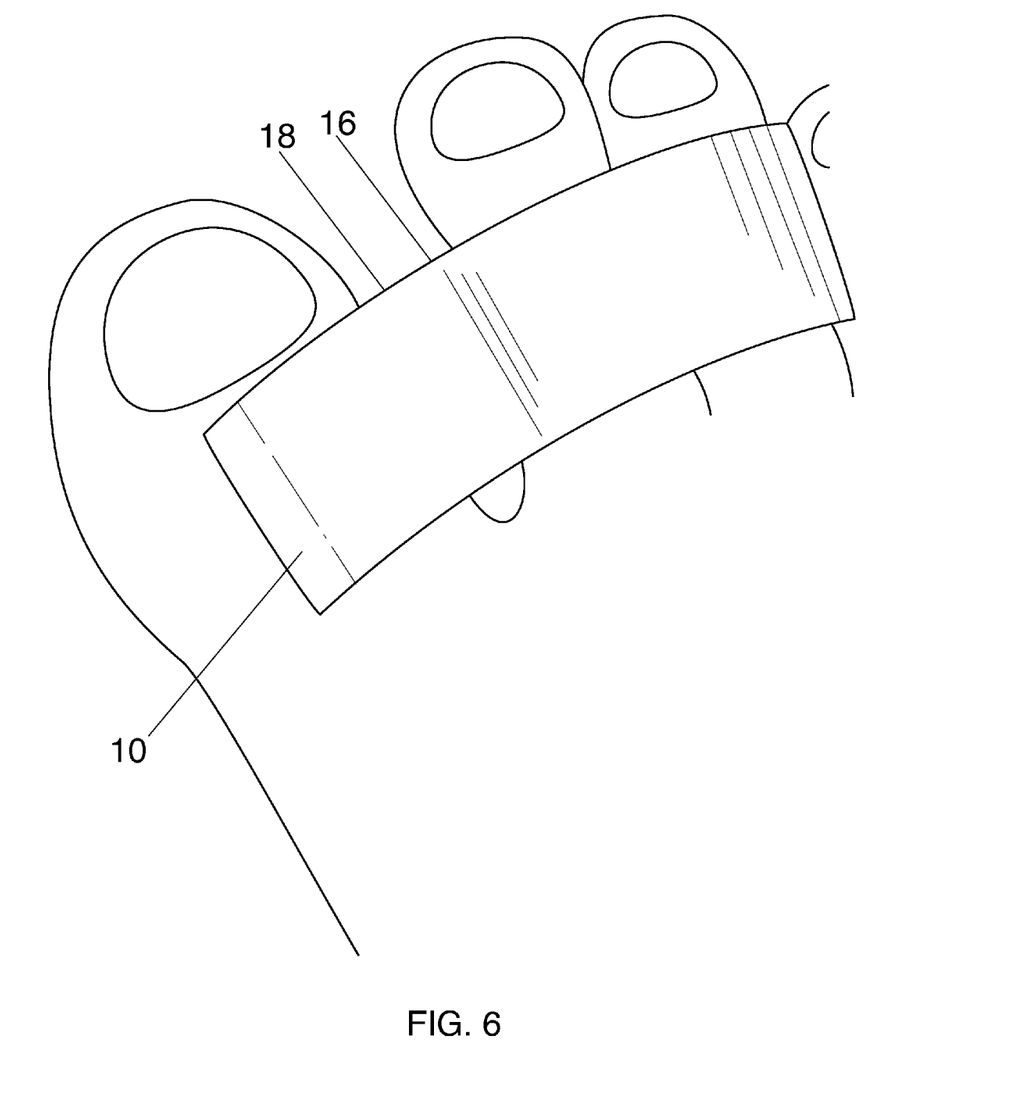
FIG. 6—Top of foot view with the inventive subject matter attached to foot between big and second toes.

Now referring to FIG. 6 that illustrates a top view of the inventive subject matter with a shaped pliable material 10, an adjustable stretch width section 16, and a removable stretch width section 18, placed in such a manner to separate the hallux from the second toe.

Figure 7:
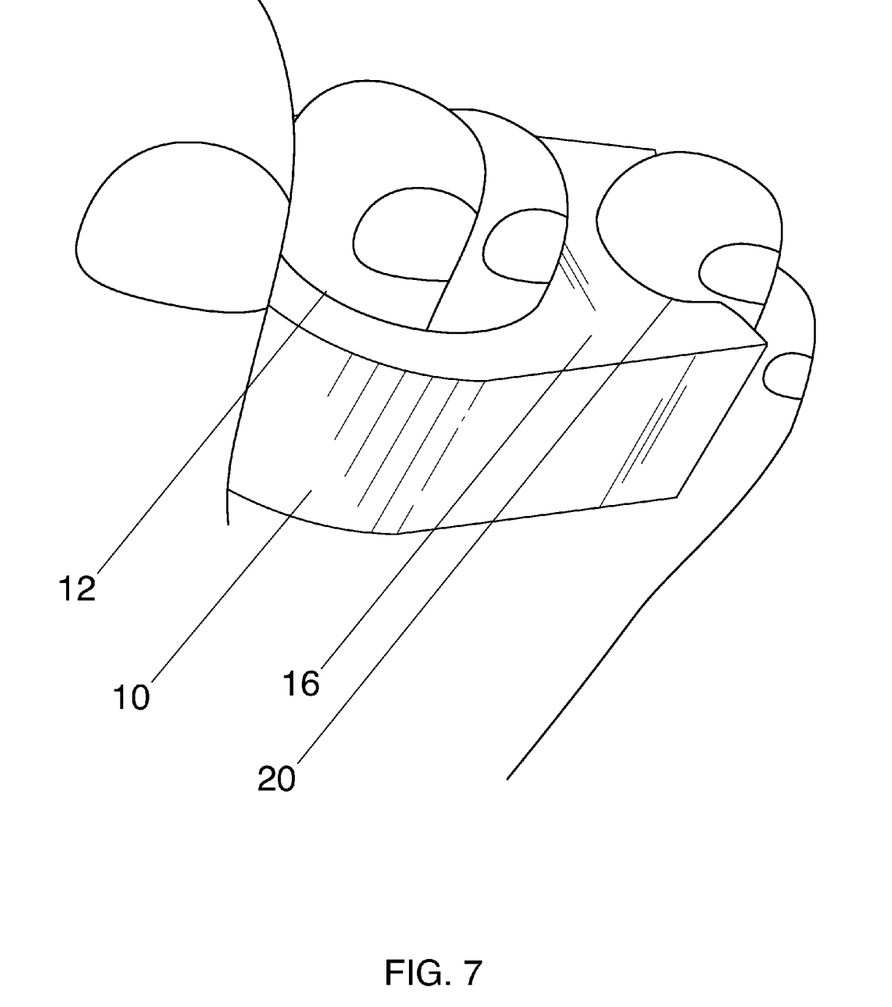
FIG. 7—Side of foot view of the inventive subject matter with removable stretch width section removed attached to foot between third and fourth toes.

Now referring to FIG. 7 that illustrates a front top view of the inventive subject matter with a shaped pliable material 10 with a shaped opening 12, the removable shaped opening 14 removed, an adjustable stretch width section 16, a removable stretch width section 18, and the removable stretch cut 20. In this configuration the second and third toe are placed together and separated from the hallux and the fourth toe.

Figure 8A:
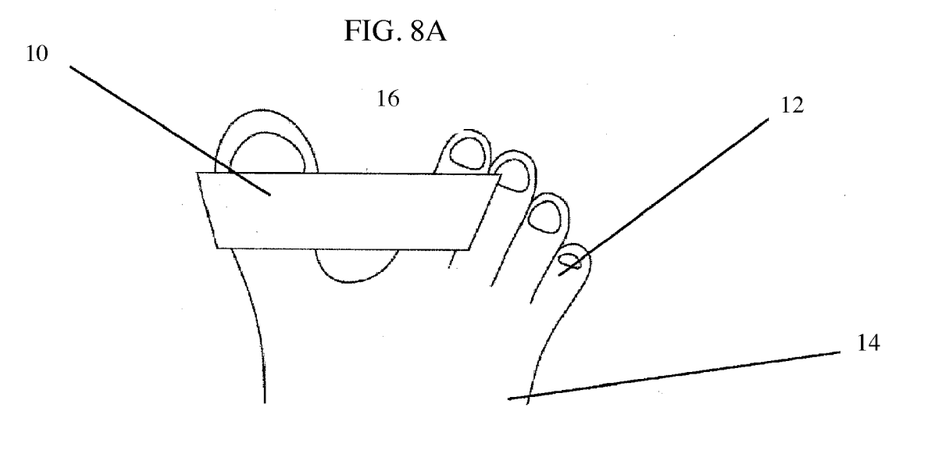
FIG. 8a and FIG. 8b—Top and front view respectively of the inventive subject matter.
Figure 8B:
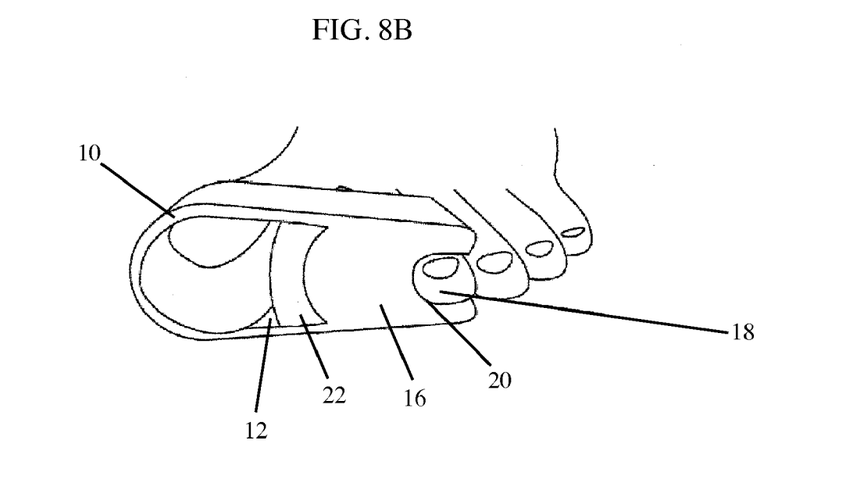

Now referring to FIG. 8A that illustrates a shaped pliable material 10 attached to the big toe of a right foot with the adjustable stretch width section 16 stretching the opening between the big toe and the second toe beyond the natural, unstretched width between these two toes. FIG. 8B illustrates a shaped pliable material 10 with a shaped opening 12, attached to the second and third toes of a left foot with the removable stretch width section 18 removed stretching the opening between the third and fourth toes beyond the natural, unstretched width between these two toes.

FIGS. 8A and 8B show that placing the shaped pliable material 10 between the two toes of either a right or left foot by inserting one or more toes into the shaped opening 12 and having the stretch width cut 20 or the half-circle indentation 22 rest up against an adjacent toe stretches the space between these toes wider than the natural, unstretched width between these toes via the adjustable stretch width section 16. By removing the removable stretch width section 18 the adjustable stretch width section 16 can vary in width depending on how much stretch is desired in between any two toes. When a foot is at rest, the stretch between two adjacent toes provided by the reversible toe manipulation device separates these toes and reduces pressure and friction and any foot pain that may be caused by malformed toes.

The adjustable stretch width section 16 between the shaped opening 12 and the half-circle indentation 22 is approximately 1". The adjustable stretch width section 16 may also range in widths, from 0.25" to 2.0", to support various toe geometries. The removable stretch width section 18 may also range in widths, from 0.25" to 1.75". The depth of the toe stretch device is approximately 1", but may also range from 0.25" to 2.0" in depth depending on the length of the toes.

The shaped pliable material 10 can be made from any pliable material that is safe to be worn against human skin. Examples of such materials are polyurethane foam, polystyrene, or any product which exhibits properties of expandability and compressibility similar to the aforementioned products. The material may also be made from hydrophilic polyurethane cosmetic foam, commonly referred to as non-latex foam.

The reversible toe manipulation device is reversible and its function is to provide separation and/or stretch capabilities equally to both feet.

All patent and non-patent literature cited herein is hereby incorporated by reference in its entirety for all purposes.

I claim:

1. A pliable toe manipulation device for at least two toes of the human foot, each foot having a hallux comprising:
    a parabolic shaped member, the member having a closed first end and an open second end;
    a shaped opening proximate to the first end, the shaped opening capable of receiving the hallux, wherein the shaped opening forms a ring around the hallux;
    a removable ring adapted to conform to an inner circumference of the shaped opening, wherein the removable ring reduces a diameter of the shaped opening;
    wherein the open end is capable of receiving a second toe most proximate to the hallux;
    wherein the toe manipulation device is reversible such that the shaped opening is adapted to receive the second and a third toe most proximate to the hallux, and the open end is adapted to receive the hallux.

2. The pliable toe manipulation device as described in claim 1 wherein the open second end is a half circular opening.

3. The pliable toe manipulation device as described in claim 1 wherein a removable stretch cut is located between the shaped opening and the open end.

4. The pliable toe manipulation device as described in claim 1 wherein the parabolic shaped member and the removable ring are fabricated from material that is safe to be worn against human skin.

5. The pliable toe manipulation device as described in claim 1 wherein parabolic shaped member and the removable ring are fabricated from foam.

6. The pliable toe manipulation device as described in claim 5 wherein said foam is selected from a group comprising polystyrene, polyurethane, extruded polyurethane, and copolymers.

7. The pliable toe manipulation device as described in claim 5 wherein said foam is hydrophilic polyurethane.

8. The pliable toe manipulation device as described in claim 5 wherein said foam is a non-irritant to the skin.

9. The pliable toe manipulation device of claim 1 wherein the removable stretch cut is formed in a removable stretch width section.

10. The pliable toe manipulation device of claim 1, wherein the shaped opening is approximately 0.25 to 2.0" in depth; the adjustable stretched width section is approximately 0.25 to 2.0" in depth; and the half circle indentation is approximately 0.25 to 2.0" in depth.

11. The pliable toe manipulation device as described in claim 1 wherein the shaped opening is capable of receiving the second and third toe and the open end is capable of receiving a fourth toe.

* * * * *